US012329355B2

(12) United States Patent
Viering et al.

(10) Patent No.: US 12,329,355 B2
(45) Date of Patent: Jun. 17, 2025

(54) MEDICAL DEVICE ASSEMBLY AND RELATED METHODS

(71) Applicant: Boston Scientific Scimed, Inc., Maple Grove, MN (US)

(72) Inventors: Kirsten Viering, Newton, MA (US); Russell Dresher, Hudson, MA (US); Paul Aquilino, Walpole, MA (US); Ryan Foss, Gorham, ME (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/352,486

(22) Filed: Jul. 14, 2023

(65) Prior Publication Data
US 2023/0355080 A1  Nov. 9, 2023

Related U.S. Application Data

(63) Continuation of application No. 17/562,232, filed on Dec. 27, 2021, now Pat. No. 11,737,652, which is a
(Continued)

(51) Int. Cl.
*A61B 1/00* (2006.01)
*A61B 1/05* (2006.01)
(Continued)

(52) U.S. Cl.
CPC ...... *A61B 1/00114* (2013.01); *A61B 1/00006* (2013.01); *A61B 1/0011* (2013.01);
(Continued)

(58) Field of Classification Search
CPC ............ A61B 1/00018; A61B 1/00112; A61B 1/00114; A61B 1/00117;
(Continued)

(56) References Cited

U.S. PATENT DOCUMENTS 4,754,328 A   6/1988   Barath et al.
4,862,258 A   8/1989   Kidawara et al.
(Continued)

FOREIGN PATENT DOCUMENTS

JP   2002-112959 A   4/2002
JP   2003116783 A    4/2003
(Continued)

OTHER PUBLICATIONS

International Search Report and Written Opinion cited in PCT/US2015/067419, dated Apr. 14, 2016, 12 pages.
(Continued)

*Primary Examiner* — Ryan N Henderson
*Assistant Examiner* — Pamela F Wu
(74) *Attorney, Agent, or Firm* — Bookoff McAndrews PLLC

(57) ABSTRACT

The present disclosure is directed to a medical device assembly. The medical device assembly described herein may include a medical device and a control unit. The medical device may include an imaging apparatus, an electrical wire coupled to the imaging apparatus, an illumination device, an illumination connector coupled to the illumination device, and a connector coupled to the electrical wire and the illumination connector. The control unit may include an electrical interface, a light source, and a port, wherein the port is configured to receive the connector to operatively couple the electrical wire to the electrical interface, and to operatively couple the illumination connector to the light source, the connector being removably attachable to the port.

16 Claims, 3 Drawing Sheets

Related U.S. Application Data continuation of application No. 16/571,327, filed on Sep. 16, 2019, now Pat. No. 11,241,143, which is a continuation of application No. 14/978,638, filed on Dec. 22, 2015, now Pat. No. 10,463,234.

(60) Provisional application No. 62/097,438, filed on Dec. 29, 2014.

(51) Int. Cl.
  *A61B 1/06* (2006.01)
  *A61B 1/07* (2006.01)

(52) U.S. Cl.
  CPC ...... *A61B 1/00124* (2013.01); *A61B 1/00126* (2013.01); *A61B 1/05* (2013.01); *A61B 1/0684* (2013.01); *A61B 1/07* (2013.01)

(58) Field of Classification Search
  CPC  A61B 1/00121–00124; A61B 1/00126; A61B 1/0011; A61B 1/05; A61B 1/07; A61B 1/00119
  USPC .................................................. 600/110, 132
  See application file for complete search history.

(56) References Cited

U.S. PATENT DOCUMENTS

| | | |
|---|---|---|
| 5,717,806 A | 2/1998 | Pileski et al. |
| 6,099,465 A | 8/2000 | Inoue |
| 2001/0008414 A1 | 7/2001 | Kobayashi et al. |
| 2003/0133011 A1 | 7/2003 | Amling et al. |
| 2005/0197536 A1 | 9/2005 | Banik et al. |
| 2006/0116550 A1* | 6/2006 | Noguchi ............ A61B 1/00121 600/131 |
| 2007/0093688 A1 | 4/2007 | Enomoto |
| 2009/0215322 A1 | 8/2009 | Omori |
| 2009/0216086 A1 | 8/2009 | Omori |
| 2009/0269962 A1* | 10/2009 | Miller ................ H01R 13/6275 439/345 |
| 2010/0022829 A1 | 1/2010 | Irion et al. |
| 2010/0178014 A1 | 7/2010 | Iwamizu et al. |
| 2011/0208004 A1 | 8/2011 | Feingold et al. |
| 2012/0041267 A1 | 2/2012 | Benning et al. |
| 2012/0100729 A1* | 4/2012 | Edidin ................ H01R 13/622 439/38 |
| 2013/0035550 A1 | 2/2013 | Watanabe et al. |
| 2013/0113906 A1 | 5/2013 | Saito |
| 2013/0172670 A1 | 7/2013 | Levy et al. |
| 2014/0073852 A1 | 3/2014 | Banik et al. |
| 2014/0328063 A1 | 11/2014 | Nishio et al. |
| 2015/0244126 A1* | 8/2015 | Carnevali ............. H01R 31/06 439/527 |

FOREIGN PATENT DOCUMENTS

| | | |
|---|---|---|
| JP | 2005-80819 A | 3/2005 |
| JP | 2005279253 A | 10/2005 |
| JP | 2006-218292 A | 8/2006 |
| JP | 2006-521882 A | 9/2006 |
| JP | 2008048905 A | 3/2008 |
| JP | 2014-113350 A | 6/2014 |
| WO | 2011092956 A4 | 8/2011 |
| WO | 2011/114957 A1 | 9/2011 |

OTHER PUBLICATIONS

Extended European search report in corresponding European Application No. 21183866.9, dated Nov. 9, 2021 (9 pages).

\* cited by examiner

MEDICAL DEVICE ASSEMBLY AND RELATED METHODS

CROSS-REFERENCE TO RELATED APPLICATIONS

This application is a continuation of U.S. application Ser. No. 17/562,232, filed Dec. 27, 2021, which is a continuation of U.S. application Ser. No. 16/571,327, filed Sep. 16, 2019, now U.S. Pat. No. 11,241,143, issued on Feb. 8, 2022, which is a continuation of U.S. application Ser. No. 14/978,638, filed Dec. 22, 2015, now U.S. Pat. No. 10,463,234, issued on Nov. 5, 2019, which claims the benefit of U.S. Provisional Application No. 62/097,438, filed Dec. 29, 2014, the disclosures of which are incorporated herein by reference in their entireties.

TECHNICAL FIELD

The present disclosure relates generally to medical devices, and more particularly to medical device assemblies and related methods. For example, aspects of the present disclosure may relate to single use, single connector medical devices connected to a single control unit, and related methods.

BACKGROUND

Endoscopic visualization may be used to diagnose and/or treat any number of conditions in the gastric, pulmonary, and urologic tracts. Endoscopes may be used to not only navigate to a target site, but also to provide adequate visualization at the target site for diagnosis and/or treatment.

Typical endoscopic systems may include a reusable endoscope, as well as separate pieces of capital equipment. For example, the capital equipment of a traditional endoscopic system may include an image processing unit and a separate light source unit. In some endoscopes, glass fiber bundles may transmit light from the proximal end, where light may be introduced from the light source, to the distal end of the endoscope. This may have a number of disadvantages. A reusable endoscope may require cleaning/sterilization following every procedure. Every cleaning cycle may potentially lead to damage of the endoscope, possibly necessitating expensive repairs. In addition, there may be a risk of reusing incorrectly/insufficiently cleaned endoscopes.

Furthermore, prior to use, the endoscope may be connected to the capital equipment. That may entail making multiple connections: an electrical connection to transmit image or video signals from the endoscope to the image processing unit, and an illumination connection to transmit light from the light source to the endoscope. Establishing multiple connections may require more user interaction and setup time. Having multiple separate units of capital equipment may also require more space within a facility.

SUMMARY

Examples of the present disclosure include medical device assemblies and methods. In one example, a medical device assembly may include a medical device and a control unit. The medical device may include an imaging apparatus, an electrical wire coupled to the imaging apparatus, an illumination device, an illumination connector coupled to the illumination device, and a connector coupled to the electrical wire and the illumination connector. The control unit may include an electrical interface, a light source, and a port, wherein the port is configured to receive the connector to operatively couple the electrical wire to the electrical interface, and to operatively couple the illumination connector to the light source, the connector being removably attachable to the port.

Examples of the medical device assembly may additionally and/or alternatively include one or more other features. For example, the illumination connector may include at least one optical fiber configured to transmit light through the medical device. Alternatively or additionally, the light source may include at least one light emitting diode configured to transmit light into the illumination connector. The control unit may include a processing unit coupled to the electrical interface, the processing unit being configured to receive imaging data from the imaging apparatus, through the electrical wire and the electrical interface. The connector may include a single cable, the electrical wire and the illumination connector may be at least partially received within the cable, and the control unit includes a single housing containing the electrical interface, the light source, and the processing unit. The illumination connector may be a first illumination connector, the illumination device may be a first illumination device, and the medical device may include a second illumination connector coupled to a second illumination device. The medical device may be an endoscope. Additional or alternatively, the imaging apparatus may be located at a distal end of the endoscope.

In another example, an endoscopic system may include an endoscope and a control unit. The endoscope may include an elongated shaft having a proximal end and a distal end, an imaging apparatus at the distal end of the elongated shaft, an electrical wire coupled to the imaging apparatus, the electrical wire extending through the elongated shaft, an illumination device at the distal end of the elongated shaft, an illumination connector coupled to the illumination device, the illumination connector extending through the elongated shaft, and a connector receiving at least a portion of the electrical wire and at least a portion of the illumination connector. The control unit may include an electrical interface, a light source, and a socket, wherein the socket is configured to receive the connector to operatively couple the electrical wire to the electrical interface, and to operatively couple the illumination connector to the light source, the connector being removably attachable to the socket.

Examples of the endoscopic system may additionally and/or alternatively include one or more other features. For example, the illumination connector may extend from a distal end of the endoscope to a proximal end of the connector. The illumination connector may include at least one optical fiber. The illumination device may be located at a distalmost end of the endoscope. The light source may include a light emitting diode. The imaging apparatus may be located at a distalmost end of the endoscope. Additionally or alternatively, the illumination connector may be a first illumination connector, the illumination device may be a first illumination device, and the endoscope may include a second illumination connector coupled to a second illumination device.

In one example, a method of connecting a medical device to a control unit may include: coupling a connector on the medical device to a port on the control unit. Coupling a connector on the medical device to a port on the control unit may include operatively coupling an illumination connector in the connector to a light source in the control unit, allowing light to be transmitted from the light source into the illumination connector, and from the illumination connector to an illumination device in the medical device, and operatively coupling an electrical wire in the connector to an electrical interface in the control unit, allowing electrical current to flow from the electrical interface to an imaging apparatus in the medical device, and allowing imaging data to flow from the imaging apparatus to the electrical interface.

Examples of the method of connecting a medical device to a control unit may additionally and/or alternatively include one or more other features. For example, the illumination connector and the light source may be operatively coupled at the same time that the electrical wire and the electrical interface are operatively coupled. The connector may be removably attachable to the port. The connector may be fixedly attached to a handle of the medical device. Additionally or alternatively, operatively coupling the illumination connector to the light source may include operatively coupling a plurality of illumination connectors in the connector to one or more light sources.

BRIEF DESCRIPTION OF THE DRAWINGS

The accompanying drawings, which are incorporated in and constitute a part of this specification, illustrate various examples and together with the description, serve to explain the principles of the disclosure.

DETAILED DESCRIPTION

Reference will now be made in detail to aspects of the disclosure, examples of which are illustrated in the accompanying drawings. Wherever possible, the same reference numbers will be used throughout the drawings to refer to the same or like parts. When used herein, the term "approximately" may indicate a range of values within +/−5% of a stated value.

Overview

Examples of the present disclosure relate to a medical device assembly and related methods. The medical device assembly described herein may allow the positioning of relatively inexpensive components/equipment within an endoscope, and more expensive components/equipment within a control unit. To address the disadvantages of having multiple separate pieces of capital equipment, as well as having to establish multiple separate connections for light and electricity, the electrical and illumination connections may be combined into one connection.

Detailed Examples

Figure 1:
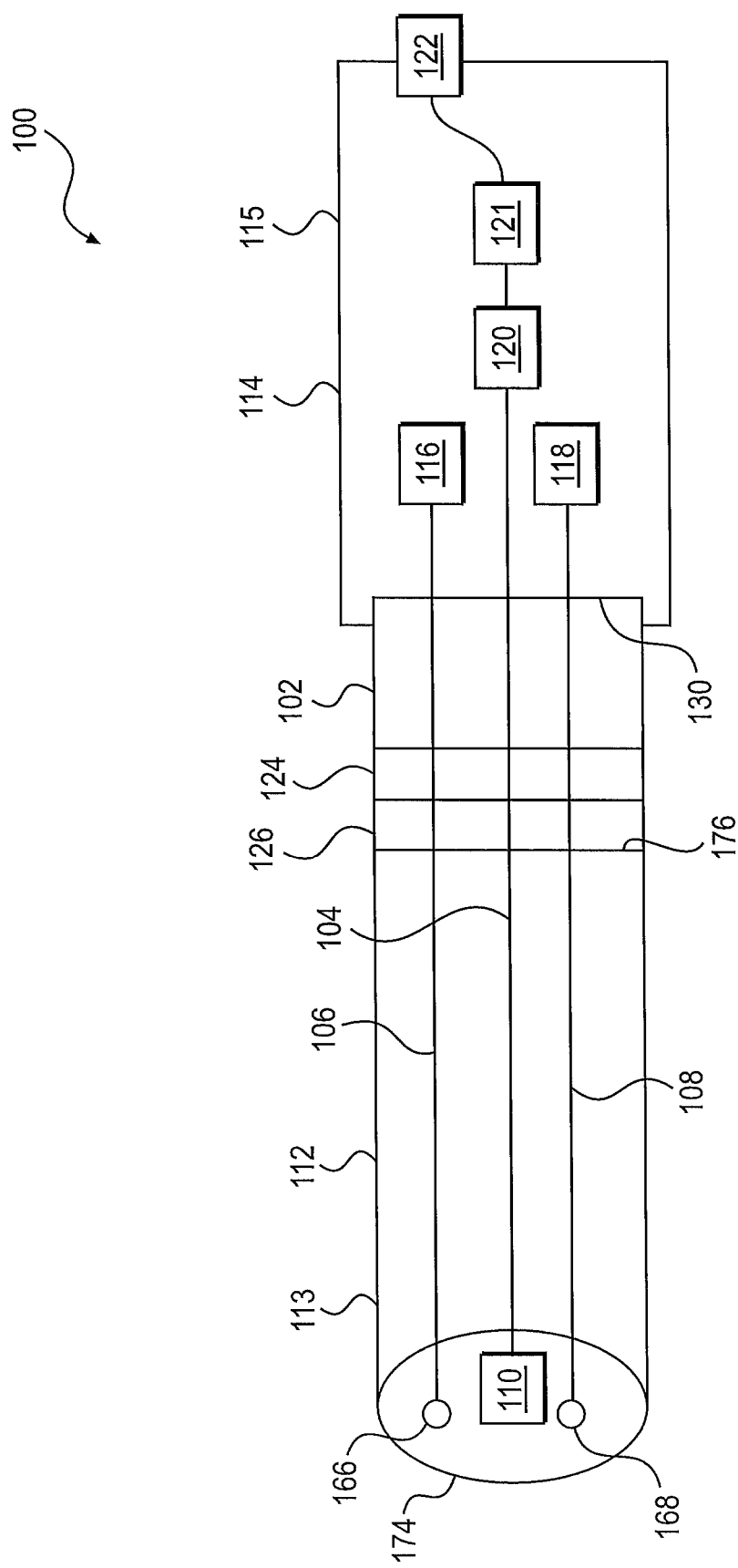
FIG. 1 is a schematic side view of a medical device assembly, according to aspects of the present disclosure.

FIG. 1 illustrates an exemplary medical device 100. Medical device 100 may include an endoscope 112, a control unit 114, and a connector 102 connecting endoscope 112 and control unit 114. FIG. 1 is merely exemplary and any of endoscope 112, control unit 114 and/or connector 102 may be used alone, in combination, and/or with other devices. For example, endoscope 112 may be connected to control units with different configurations and/or equipment than control unit 114. Similarly, control unit 114 may be used with any suitable device, not just endoscope 112. For example, control unit 114 may be used with a different endoscope, a catheter, a probe, and/or any other device that uses one of, but not necessarily all of, electrical power, an imaging apparatus, and/or a light source. While endoscope 112 may be designed to be used once and discarded, due to its relatively inexpensive cost, it is contemplated that endoscope 112 may be used multiple times if desired.

A. Endoscope

Endoscope 112 may include shaft 113. Endoscope 112 may have a distal end 174 and a proximal end 176, with one or more electrical wires 104 and/or one or more of illumination connectors 106 and 108 extending therebetween. Proximal end 176 may be coupled to connector 102. For example, proximal end 176 may be coupled to connector 102 by a handle 126 of endoscope 112, and/or by an umbilicus or connector cable 124 extending to connector 102. In one example, connector 102 may be fixedly attached to the proximal end 176 of endoscope 112. In another example, connector 102 may be removably attached to endoscope 112.

Endoscope 112 may include one or more illumination devices at its distal end 174. For example, as shown in FIG. 1, endoscope 112 may have two illumination devices 166 and 168. Illumination devices 166 and 168 may be the distal ends of illumination connectors 106 and 108, respectively. In one example, illumination connectors 106 and 108 may include an optical fiber, a fiber bundle, or a combination thereof. Rather than using a glass fiber bundle to transmit light from the proximal end 176 to the distal end 174 of the endoscope 112, light may be transmitted into a single or a few large diameter plastic optical fibers with a high numerical aperture. Plastic optical fibers may be less expensive than glass fibers, lowering the cost of production for the endoscope 112. Handling and assembling single fibers may be easier as compared to fiber bundles, thereby further lowering the cost of production by reducing manufacturing time and potentially increasing yield.

Plastic optical fibers are available with a number of different numerical apertures and diameters. The larger the numerical aperture and the diameter of the fibers, the more light may be transmitted by the fibers. Based on dimensional constraints within the body of the endoscope 112, it may be advantageous to select the thinnest plastic optical fiber that may be capable of providing adequate illumination. Light may be directed into illumination connectors 106 and 108 from one or more light sources located external to endoscope 112, e.g., one or more light sources in control unit 114. Exemplary light sources will be described below.

Distal end 174 of endoscope 112 may include an imaging apparatus 110 connected to electrical wires 104. Imaging apparatus 110 may include an imaging sensor, such as a charge-coupled device (CCD) or complementary metal-oxide semiconductor (CMOS) imaging sensor. It is also contemplated that imaging apparatus 110 may include a camera unit.

Electrical wires 104 may provide power from a source external to endoscope 112, e.g., a wall socket or source within control unit 114, to imaging apparatus 110. Electrical wires 104 may additionally or alternatively transmit data from the imaging apparatus 110 to a processor. In one example, the processor may be internal to the endoscope 112. For example, the processor may be housed within handle 126. In another example, the processor may be external to endoscope 112. For example, the data may be transmitted through electrical wires 104 to connector 102, and into a processing unit 121 in the control unit 114.

B. Control Unit

As illustrated in the example shown in FIG. 1, control unit 114 may include, but is not limited to, one or more of light sources 116 and 118, a port or socket 130, an electrical interface 120, processing unit 121, and/or a data output 122. These components may be within the same housing 115 of control unit 114. Control unit 114 may be a single piece of capital equipment containing the aforementioned components.

Socket 130 may provide access from the exterior of housing 115 of control unit 114 to the interior of housing 115, and/or access to the components disposed within housing 115. For example, socket 130 may allow operative coupling of illumination connectors 106 and 108 to light sources 116 and 118. Additionally or alternately, socket 130 may allow operative coupling of electrical wires 104 to electrical interface 120, processing unit 121, and/or data output 122. Socket 130 may be attached to control unit 114 by, for example, welding, a locking configuration, use of an adhesive, or integral forming with control unit 114. Additionally or alternatively, socket 130 may be embedded within a side surface of control unit 114 and/or detachable from control unit 114. Socket 130 will be described in further detail below with respect to FIGS. 3 and 4.

Light sources 116 and 118 may be coupled to illumination connectors 106 and 108, respectively. Alternatively, illumination connectors 106 and 108 may both be coupled to one of light sources 116 and 118. Light sources 116 and 118 may be removable attached to connectors 106 and 108. Light sources 116 and 118 may include any suitable light source. In some examples, any wavelength of light, including, but not limited to, white light and/or fluorescent light may be emitted by the light sources 116 and 118. In one example, light sources 116 and 118 may include halogen or xenon light sources. In another example, light sources 116 and 118 may include light-emitting diodes (LEDs). Light sources 116 and 118 may include a combination of light sources. For example, light source 116 may include a halogen light, and light source 118 may include an LED. One of light sources 116 and 118 may include a combination of light sources. For example, light source 116 may include a combination of halogen, xenon, and/or LED sources, all coupled to a single illumination connector 106. Light sources 116 and 118 are merely exemplary. Control unit 114 may have any suitable number of, and type of, light sources.

Electrical interface 120 may receive data from any suitable device. In one example, electrical interface 120 may be removably coupled to electrical wires 104 that extend within connector 102. In such an example, data from imaging apparatus 110, located at the distal end 174 of endoscope 112, may be transmitted to electrical interface 120 through electrical wires 104. The electrical interface 120 may have any suitable configuration. In one example, electrical interface 120 may include 16 spring loaded pogo pins (not shown) located within socket 130, and corresponding pads (not shown) for the pins on the connector 102. This configuration may allow for 16 separate electrical connections. In one example, the configuration may allow for the supply of power and ground to the imaging apparatus 110, and/or data transfer between imaging apparatus 110 and control unit 114, including low voltage differential signaling, imaging apparatus calibration data, and/or image or video data.

Processing unit 121 may be configured to process any information, including, but not limited, to information for calibrating data from imaging apparatus 110, determining brightness of a region, adjusting brightness of light sources 116 and 118, determining the size and/or composition of an object viewed by the imaging apparatus 110, creating and adjusting an output image from imaging apparatus 110, and/or any other suitable form of processing. In one example, processing unit 121 may provide and regulate power to light sources 116 and 118 and/or transmit image information to a monitor (not shown) at or through data output 122. It is also contemplated that the processing unit 121 may process information unrelated to light source 116 and 118 and/or imaging apparatus 110. For example, the processing unit 121 may determine the best path to a target area for endoscope 112, or any other suitable device, and steer the device to the target area. In another example, endoscope 112, or any other suitable device, may extract samples from a target area, and processing unit 121 may determine one or more characteristics (e.g., composition) of the samples.

Data output 122 may include any device for outputting the data processed by processing unit 121. For example, data output 122 may include a monitor (not shown) embedded in a side surface of, attached to, and/or connected to control unit 114. Data output 122 may include a port or cable (not shown) that is configured to connect to the monitor or a separate computing unit (not shown). In one example, the data output 122 may produce or otherwise communicate a still image or video images. In such an example, these images may be displayed on the monitor via data output 122.

C. Connector

Connector 102 may be fixedly attached or removably attached to the proximal end 176 of shaft 113, and/or to handle 126. Electrical wires 104, illumination connector 106 and/or illumination connector 108 may extend out of shaft 113 to the distal end of connector 102, and through the length of connector 102. Connector 102 may be attached to endoscope 112 and/or control unit 114 by, for example, fasteners, cables, welding, a locking configuration, use of an adhesive, or integrally forming with endoscope 112 and/or control unit 114. Additionally or alternatively, connector 102 may be attached to handle 126 of endoscope 112 by an umbilicus or connector cable 124.

Figure 2:
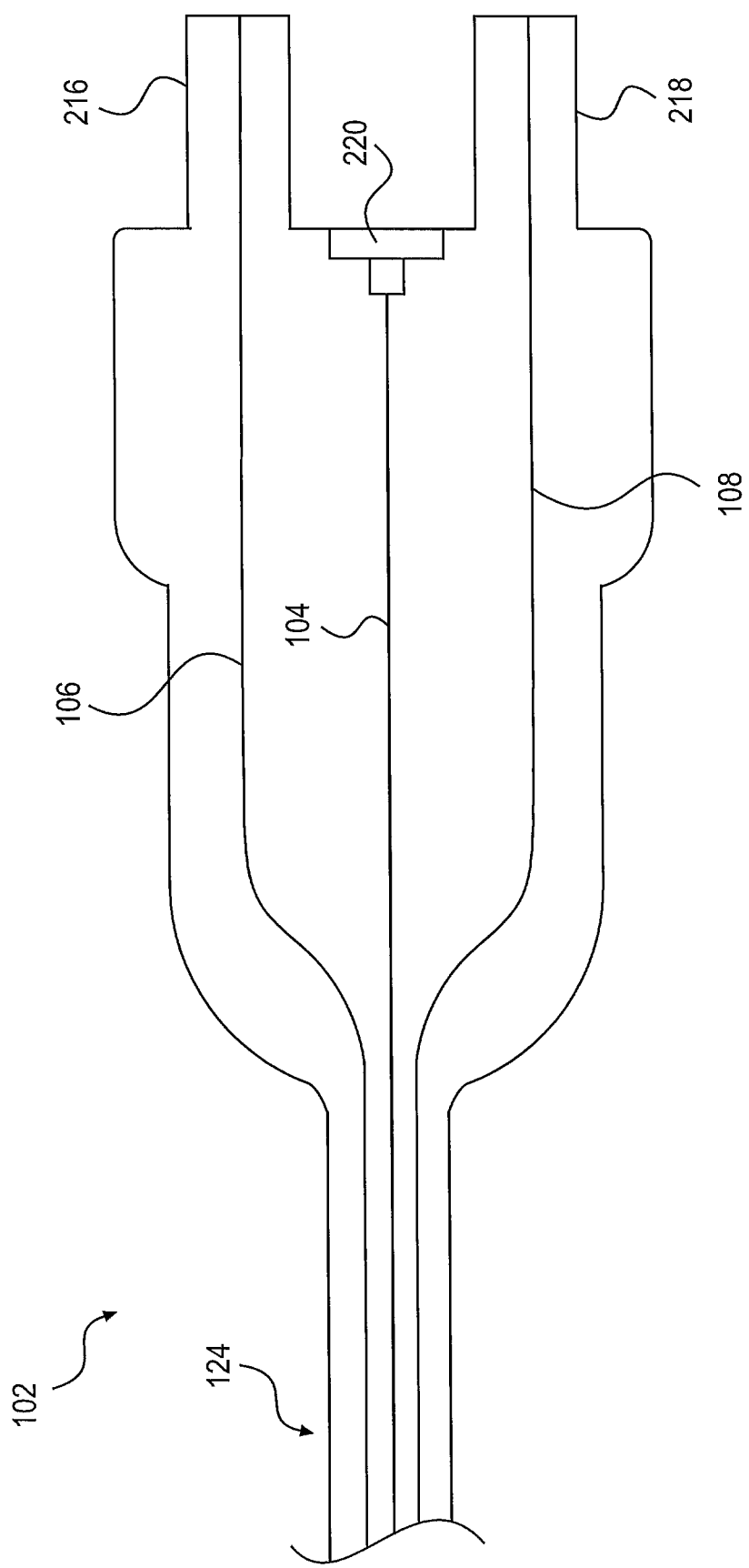
FIG. 2 is a schematic side view of a connector, according to aspects of the present disclosure.

An example of connector 102 is illustrated in FIG. 2. Connector 102 may include, but is not limited to, connector cable 124, one or more electrical wires 104, one or more of illumination connectors 106 and 108, one or more of prongs 216 and 218 and/or an electrical connection 220. In one example, connector cable 124 may be connected to the distal end of connector 102. Connector cable 124 may be connected to the proximal end of endoscope 112. For example, connector cable 124 may be connected to handle 126 at the proximal end 176 of shaft 113. Electrical wires 104 and/or illumination connectors 106 and 108 may be disposed within and/or extend the length of connector cable 124. Electrical wires 104 and/or illumination connectors 106 and 108 may extend the length of connector 102. In one example, the length of connector cable 124 may be less than approximately 4.6 meters. It is contemplated that connector 102 may be the only connector for electrical and illumination connections between endoscope 112 and control unit 114.

Electric wires 104 may extend to electrical connection 220. In one example, electrical connection 220 may be placed in electric communication with electrical interface 120, illustrated in FIG. 1. For example, electrical connection 220 may include one or more contacts or pads (not shown) that may be removably coupled to one or more contacts or pins (not shown) of electrical interface 120.

In one example, and as shown in FIG. 2, electrical wires 104 may extend along a longitudinal axis of connector 102. For example, electrical wires 104 may be located between illumination connectors 106 and 108. This may aid in correctly aligning illumination connectors 106 and 108 to light sources 116 and 118, which may be spaced apart within control unit 114. Separating light sources 116 and 118 may be desired for a variety of reasons including, for example, accommodating the sizes of the light sources 116 and 118, avoiding the possibility of crossing light paths of light sources 116 and 118, and/or helping to disperse heat radiating from the light sources 116 and 118.

Illumination connectors 106 and 108 may extend through prongs 216 and 218, respectively. Prongs 216 and 218 may connect to control unit 114. Prongs 216 and 218 may be sized to be received by control unit 114. For example, prongs 216 and 218 may be approximately 5 cm to 10 cm long. Light sources 116 and 118 may be approximately 1.25 cm to 4 cm apart. In such an example, prongs 216 and 218 may be configured so that illumination connectors 106 and 108 are aligned with the light sources 116 and 118 (e.g., prongs 216 and 218 may be approximately 1.25 cm to 4 cm apart). If, for example, light sources 116 and 118 may be approximately 2.5 cm apart, illumination connectors 106 and 108, and prongs 216 and 218, may also be approximately 2.5 cm apart at the location where they are received by control unit 114. The tolerances for aligning an illumination connector with a light source may be between approximately 0.10 mm and approximately 1.0 mm or preferably approximately 0.25 mm. The tolerances may depend on the amount of light required. For example, the less light necessary to adequately illuminate the desired area, the larger the tolerances.

While two prongs 216 and 218 are shown in FIG. 2, it should be understood that a single prong, or more than two prongs, may be present on connector 102. A single prong may be used in an example where endoscope 112 includes a single light source and a single illumination connector. More than two prongs may be used in an example where endoscope 112 includes more than two light sources and more than two illumination connectors. In some examples, a prong may contain more than one illumination connector. Prong 216 and/or prong 218 may assist with aligning electrical connector 220 with electrical interface 120, when connector 120 is attached to control unit 114.

D. Port/Socket

Figure 3:
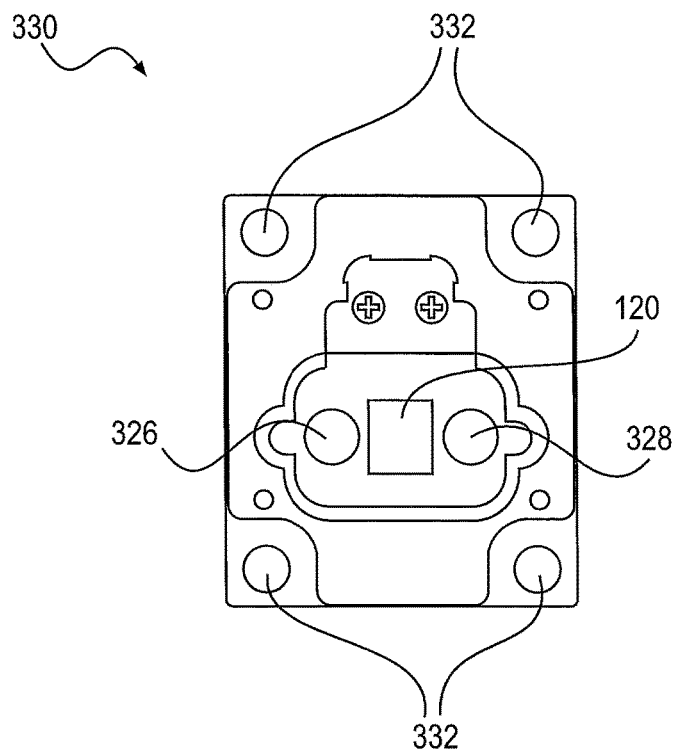
FIG. 3 is a front view of a port or socket for connecting to the connector of FIG. 2, according to aspects of the present disclosure.

An exemplary port or socket 330 is illustrated in FIG. 3. Socket 130 of FIG. 1 may be similar to socket 330. Socket 330 may include, but is not limited to, fastener openings 332, illumination connector openings 326 and 328, and/or electrical interface 120. In one example, socket 330 may be attached to a side surface of control unit 114. Socket 330 may be attached to or contained within control unit 114 by inserting fasteners through fastener holes 332. For example, socket 330 may be attached by inserting screws through fastener holes 332.

Connector openings 326 and 328 may be configured to receive prongs 216 and 218, respectively. Connector openings 326 and 328 and prongs 216 and 218 may have a friction fit to help maintain coupling. In some examples, friction fit may also be achieved between other elements of socket 330 and connector 102. Connector openings 326 and 328 may allow illumination connectors 106 and 108, in prongs 216 and 218, to access control unit 114 and align with light sources 116 and 118 of FIG. 1. Once aligned, further insertion of prongs 216 and 218 into connector openings 326 and 328 may bring illumination connectors 106 and 108 into contact with light sources 116 and 118, such that light may be transmitted from light sources 116 and 118 into illumination connectors 106 and 108. It is contemplated that prongs 216 and 218 of connector 102 may be fully seated in connector openings 326 and 328, thereby coupling illumination connectors 106 and 108 to light sources 116 and 118, at the same time that electrical connection 220 is fully seated on, in, or against electrical interface 120 at socket 330.

Figure 4:
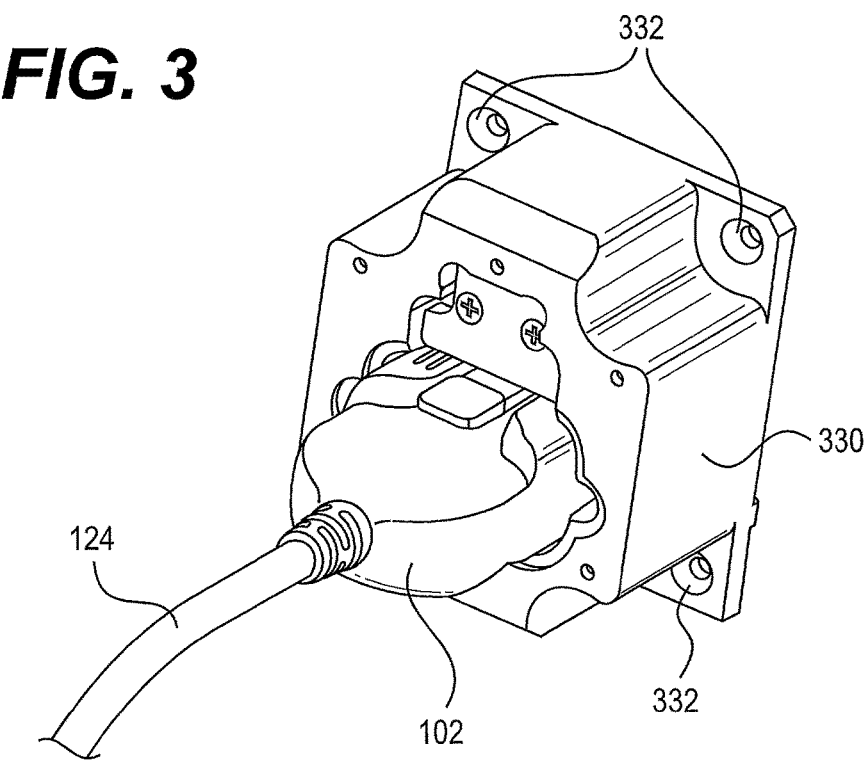
FIG. 4 is a perspective view of the connector of FIG. 2 connected to the socket of FIG. 3, according to aspects of the present disclosure.

FIG. 4 illustrates an example of socket 330 connected to connector 102. Connector cable 124 may connect connector 102 to another device, such as endoscope 112. For example, connector cable 124 may connect connector 102 to handle 126 of endoscope 112.

The many features of the disclosure are apparent from the detailed specification, and thus, it is intended by the appended claims to cover all such features of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other examples will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of connecting a medical device to a control unit, comprising:
    coupling a connector of the medical device to a port on the control unit, wherein the connector is removably coupled to the port, and wherein coupling the connector to the port includes:
        inserting a first prong of the connector into a first opening of the port, wherein the first prong includes a first illumination connector, wherein the control unit includes a first light source, and wherein, upon insertion of the first prong into the first opening, the first illumination connector is operatively coupled to the first light source;
        inserting a second prong of the connector into a second opening of the port, wherein the second prong includes a second illumination connector, wherein the control unit includes a second light source, and wherein, upon insertion of the second prong into the second opening, the second illumination connector is operatively coupled to the second light source; and
        operatively coupling an electrical wire in the connector to an electrical interface in the control unit,
    wherein the electrical interface is disposed between the first opening and the second opening such that a straight line extends through the first opening, the second opening, and the electrical interface.

2. The method of claim 1, wherein the connector is fixedly attached to a handle of the medical device.

3. The method of claim 1, wherein, upon coupling the connector of the medical device to the port on the control unit, the first illumination connector and the first light source, the second illumination connector and the second light source, and the electrical wire and the electrical interface are operatively coupled at a same time.

4. The method of claim 1, wherein the connector of the medical device is removably coupled to the port of the control unit by a friction fit.

5. The method of claim 1, wherein the connector includes an electrical connection portion, and wherein the electrical wire is electrically coupled to the electrical connection portion.

6. The method of claim 5, wherein the electrical connection portion is disposed between the first prong and the second prong.

7. The method of claim 5, wherein the electrical interface of the control unit includes at least one spring loaded pogo pin, and wherein the electrical connection portion of the connector includes at least one electrical pad corresponding to each of the at least one spring loaded pogo pin.

8. A method of coupling a first medical device to a second device, comprising:
coupling the second device to a third medical device; and
inserting a connector of the first medical device into the second device, wherein inserting the connector into the second device includes:
inserting a first prong of the connector into a first opening of the second device, wherein the first prong of the connector includes a first illumination connector, wherein the third medical device includes a first light source, and wherein, upon insertion of the first prong into the first opening of the second device, the first illumination connector is operatively coupled to the first light source;
inserting a second prong of the connector into a second opening of the second device, wherein the second prong includes a second illumination connector, wherein the third medical device includes a second light source, and wherein, upon insertion of the second prong into the second opening of the second device, the second illumination connector is operatively coupled to the second light source; and
seating an electrical connection of the connector against an electrical interface of the second device, wherein, upon seating the electrical connection against the electrical interface, data is transmitted from the first medical device to the second device,
wherein the electrical connection of the connector is between the first prong and the second prong such that a straight line extends through the first prong, the second prong, and the electrical connection.

9. The method of claim 8,
wherein the second device is a socket, wherein the third medical device is a control unit.

10. The method of claim 9, wherein the socket is coupled to the control unit by one or more fasteners.

11. The method of claim 8, wherein the electrical interface includes at least one spring loaded pogo pin, and wherein the electrical connection of the connector includes at least one electrical pad corresponding to each of the at least one spring loaded pogo pin.

12. The method of claim 8, wherein the connector of the first medical device is removably coupled to second device by a friction fit.

13. A method of coupling a medical device to a control unit, comprising:
coupling a socket to the control unit;
inserting a first prong of a connector of the medical device into a first opening of the socket, wherein the first prong of the connector includes a first illumination connector, wherein the control unit includes a first light source, and wherein, upon insertion of the first prong into the first opening of the socket, the first illumination connector is operatively coupled to the first light source;
inserting a second prong of the connector into a second opening of the socket, wherein the second prong includes a second illumination connector, wherein the control unit includes a second light source, and wherein, upon insertion of the second prong into the second opening of the socket, the second illumination connector is operatively coupled to the second light source; and
coupling an electrical connection of the connector to an electrical interface of the socket, wherein the electrical connection of the connector is between the first prong and the second prong of the connector such that a straight line extends through the first prong, the second prong, and the electrical connection.

14. The method of claim 13, wherein the connector of the medical device is removably coupled to the socket of the control unit by a friction fit.

15. The method of claim 13, wherein the socket is coupled to the control unit by one or more fasteners.

16. The method of claim 13, wherein the electrical interface of the socket includes at least one spring loaded pogo pin, and wherein the electrical connection of the connector includes at least one electrical pad corresponding to each of the at least one spring loaded pogo pin.

* * * * *